United States Patent [19]
Pollock et al.

[11] Patent Number: 5,338,841
[45] Date of Patent: Aug. 16, 1994

[54] DNA SEGMENTS CONTROLLING PRODUCTION OF XANTHAN GUM

[75] Inventors: Thomas J. Pollock; Linda Thorne, both of San Diego, Calif.

[73] Assignees: Shin-Etsu Chemical Co., Ltd., Tokyo, Japan; Shin-Etsu Bio, Inc., San Diego, Calif.

[21] Appl. No.: 825,600

[22] Filed: Jan. 24, 1992

Related U.S. Application Data

[60] Division of Ser. No. 517,551, Apr. 24, 1990, Pat. No. 5,279,961, which is a continuation of Ser. No. 180,945, Apr. 12, 1988, abandoned, which is a continuation-in-part of Ser. No. 38,302, Apr. 14, 1987, abandoned.

[51] Int. Cl.$^5$ .................... C12N 15/31; C12N 1/21
[52] U.S. Cl. .................... 536/23.7; 435/252.3
[58] Field of Search ............. 536/27, 23.7; 435/104, 435/172.3, 320.1, 252.3

[56] References Cited

PUBLICATIONS

Harding et al., *J. Bacteriol.*, vol. 169, 1987, pp. 2854–2861.
Kennedy et al., in *Progress in Industrial Microbiology*, 1984, M. E. Bushell, ed., Elsevier, Amsterdam, pp. 319–371.
Harding et al., *Abstr. Ann. Meeting of Amer. Soc. for Microbiol.*, p. 273, Abstract No. 0–64, Mar. 1986.
Beguin et al., *CRC Crit. Rev. Biotechnol.*, vol. 6, 1987, pp. 129–162.

*Primary Examiner*—Richard A. Schwartz
*Assistant Examiner*—James Ketter
*Attorney, Agent, or Firm*—McAulay Fisher Nissen Goldberg & Kiel

[57] ABSTRACT

A method of increasing xanthan gum production, comprising culturing a *Xanthomonas campestris* strain having a xanthan-increasing modification in a culture medium, wherein the modification is selected from the group consisting of (1) a mutation causing rifampicin-resistance; (2) a mutation causing bacitracin-resistance; or (3) exogenous genetic information controlling the synthesis of xanthan; and separating xanthan from the culture medium, is provided along with specific DNA sequences and *Xanthomonas campestris* strains showing increased xanthan gum production.

1 Claim, 6 Drawing Sheets

DNA SEGMENTS CONTROLLING PRODUCTION OF XANTHAN GUM

CROSS-REFERENCE TO RELATED APPLICATIONS

This is a divisional of U.S. application Ser. No. 07/517,551, filed Apr. 24, 1990, now U.S. Pat. No. 5,279,961, which is a continuation of U.S. application Ser. No. 07/180,945, filed Apr. 12, 1988, now abandoned, which is a continuation-in-part of U.S. application Ser. No. 07/038,302, filed Apr. 14, 1987 now abandoned.

BACKGROUND OF THE INVENTION

1. Field of the Invention

The present invention relates to the synthesis of xanthan gum by *Xanthomonas campestris* and particularly to methods for increasing synthesis by modifying the natural organism.

b 2. Background of the Invention

A number of microorganisms produce extracellular polysaccharides, also known as exopolysaccharides or EPS. The exopolysaccharide known as xanthan is produced by the bacterium *Xanthomonas campestris*. The strain *X. campestris* pv *campestris* is a causal agent of black rot of cruellets.

Xanthan itself is useful as a specialty polymer for a growing number of commercial applications. The exploitation of xanthan as a commercial product results from a successful screening effort by the Northern Regional Research Center to find useful water-soluble polysaccharide products to replace existing gums from plant and algal sources. The NERL discovered *X. campestris* NRRL B1459, a strain which produces a polymer that exhibits three desirable properties: (1) high viscosity at low concentrations; (2) pseudoplasticity; and (3) insensitivity to a wide range of temperature, pH, and electrolyte concentrations. Because of its special theological properties, xanthan is used in food, cosmetics, pharmaceuticals, paper, paint, textiles, and adhesives and otherwise in the oil and gas industry.

In addition, the polymer is readily produced by fermentation from D-glucose. The synthesis of xanthan is believed to be similar to exopolysaccharide synthesis by other Gram-negative bacteria, such as species of Rhizobium, Pseudomonas, Klebsiella, and Escherichia. The synthetic pathway can be divided into three parts: (1) the uptake of simple sugars and their conversion to nucleotidal derivatives; (2) the assembly of pentasaccharide subunits attached to an isopentenyl pyrophosphate carrier; and (3) the polymerization of pentasaccharide repeat units and their secretion. By comparison to the more advanced molecular genetic understanding of colanic acid synthesis by *E. coli* or alginate synthesis by *P. aeruginosa*, little is known about the genes, enzymes, or mechanisms that control the synthesis of xanthan by *X. campestris*.

Xanthan gum is usually produced by fermentation of *X. campestris* with glucose or corn syrup as the major carbon source. Although it is also possible to convert the glucose and galactose in hydrolyzed cheese whey to xanthan gum, wild-type strains of *X. campestris* utilize lactose poorly, and the whey must first be hydrolyzed enzymatically with lactase of β-galactosidase. There are some suggestions that the β-galactosidase of *X. campestris* has a low affinity for lactose, thereby accounting for the poor utilization or unhydrolyzed lactose. Attempts have been made to generate a strain of *X. campestris* that can utilize lactose more efficiently. Exogenous lac genes have been transferred into *X. campestris* using transposon Tn951 which was in turn inserted within the mobilizable broad host range plasmid RP1. However, the plasmid, and therefore the lac genes, were not stable in the absence of a plasmid-selective antibiotic. Other investigators isolated a spontaneous derivative of *X. campestris* B1459 that could convert unhydrolyzed lactose in whey to xanthan gum. However, the nature of the mutation was not known, and the strain proved to be unstable for xanthan production, losing considerable productivity within forty generations under non-selective conditions.

Other genetic manipulations of *X. campestris* are also desirable. For example, undesirable enzymes are sometimes produced that contaminate the xanthan product, limiting the usefulness of xanthan gum to a narrower range of situations than would otherwise be possible.

Accordingly, an increased understanding or the genetic control of xanthan production by *X. campestris* would be useful for improving the productivity of *X. campestris* for xanthan synthesis.

3. Description of Relevant Literature

A recent publication on the topic of molecular cloning of genes involved in the production of xanthan in Bartere et al., *Int. J. Biol. Macrotool.* (1986) 8: 372–374. A study showing that a mutation, which blocks exopolysaccharlde synthesis and prevents modulation of peas by *Rhizoblum leguminosarum*, was corrected by cloned DNA from the phytopathogen *Xanthomonas* is described in Borthakur et al., *Mol. Gen. Genet.* (1986) 203:320–323. Production of xanthan using *Xanthomonas campestris*, properties of xanthan, and commercial applications of xanthan are described in Rogovin et al. *J. Biochem. Microbiol Technol. Eng.* (1961) 3:51-63, and Kennedy et al., 1984, "Production, properties, and applications of xanthan", pp. 319–371 in M. E. Bushell (ed.), Progress in Industrial Microbiology, vol. 19, Elsevier, Amsterdam.

A number of publications have occurred after the filing of U.S. application Ser. No. 038,302 on Apr. 14, 1987, now abandoned. These include Harding et al., *J. Bacteriol.* (1987) 169:2854–1286, which describes genetic and physical analyses of a cluster of genes essential for xanthan gum biosynthesis in *X. campestris*. European Patent Application EP 0 233 019 A2, filed Jan. 29, 1987, describes a recombinant DNA plasmid for xanthan gum synthesis. Thorne et al., *J. Bacteriol.* (1987 ) 169:3593–3600, describes clustering of mutations blocking synthesis of xanthan gum by *X. eampestris*.

SUMMARY OF THE INVENTION

A method of increasing xanthan gum production is provided, which comprises culturing a *Xanthomonas campestris* strain having a xanthan-increasing modification in a culture medium, wherein said modification is selected from the group consisting of (1) a mutation causing rifampicin-resistance; (2) a mutation causing bacitracin-resistance; or (3) expressible exogenous genetic information controlling the synthesis of xanthan; and separating xanthan from the culture medium. A section of Xanthomonas chromosomal DNA containing genetic information controlling the synthesis-of xanthan is identified, which allows use of numerous techniques for increasing xanthan production such as providing multiple copies to increase xanthan production by a dosage effect and providing an inducible promoter or other method of genetic control in order to decouple xanthan production from constitutive protein synthesis. Mutations providing resistance to the indicated antibiotics can be obtained by standard techniques now that the specific antibiotic resistance factors capable of increasing xanthan production have been identified.

BRIEF DESCRIPTION OF THE DRAWINGS

The present invention will be better understood by reference to the following detailed description of specific embodiments when considered in combination with the enclosed drawings which form part of the specification, wherein.

DESCRIPTION OF SPECIFIC EMBODIMENTS

Investigations in the laboratories of the inventors have indicated that a number of modifications are available that are capable of increasing xanthan gum production from *Xanthomonas campestris* strains. Three specific genetic modifications capable of increasing xanthan production are mutations causing rifampicinresistance, mutations causing bacitracin-resistance, and the presence of exogenous genetic information controlling the synthesis of xanthan introduced into a *Xanthomonas campestris* strain.

The first two of these techniques, both of which involve utilization of a mutant strain having resistance to an antibiotic, can be carried out in a straightforward manner now that the relationship between antibiotic resistance and xanthan production has been determined.

Rifampicin is a member of the group of antibiotics known as rifamycins, produced by *Streptomyces mediterraniae*. They contain a napthalene ring system bridged between positions 2 and 5 by an aliphatic chain. Rifampicin is known to inhibit DNA-dependent RNA synthesis in prokaryotics, chloroplasts, and mitochondria. Inhibition is due to the formation of a stable complex between RNA polymerase and rifampicin. A description of rifampicin and other rifamycins is set forth in The Concise Encyclopedia of Biochemistry, Walter D. Gruyter, New York, 1983, p. 418.

Bacitracins are branched, cyclic peptides produced by various strains of *Bacillus licheniformis*. The most important of these peptides is bacitracin A, which contains a thtazoline structure synthesized from an N-terminal Isoleucine and its neighboring cystine. The known motive action for bacitracins is by interference with murein synthesis. Murein is a cross-linked polysaccharide-peptide complex of indefinite size that forms a structural constituent of the inner wall layer of all bacteria. Murein consists of linear parallel chains of up to 20 alternating residues of $\beta$-1,4-linked residues of N-acetylglucosamine and N-acetylmuramic acid, extensively cross-linked by peptides.

Resistant mutants can be prepared by culturing a *Xanthomonas campestris* strain in a culture medium containing one or both or the indicated antibiotics. Antibiotic concentrations or from 1 µg/ml to 1000 µg/ml,. preferably at least 5 µg/ml, more preferably at least 50 µg/ml, preferably no more than 500 µg/ml, more preferably no more than 250 µg/ml for rifampicin are useful as initial concentrations in the practice of the present invention. Antibiotic concentrations of from 100 $\mu$g/ml to 1000 $\mu$g/ml, preferably at least 200 $\mu$g/ml, more preferably at least 250 $\mu$g/ml, preferably no more than 500 $\mu$g/ml, more preferably no more than 400 $\mu$g/ml for bacitracin are useful as initial concentrations in the practice of the present invention. These concentrations can be adjusted upward or downward in response to observed conditions of growth and/or survival during cultivation. The remaining components of the culture medium are those normally used for Xanthomonas cultivation and include water, buffering agents such as ammonium phosphate and sodium nitrate, salts such as magnesium sulfate and calcium chloride, glucose sufficient to maintain growth, and trace minerals. Other components such as yeast extract, malt extract, peptone, and Amberex can be utilized if desired.

Selection can be made either for spontaneous mutations that survive growth in the selection media or mutations can be induced by a mutagen such as ultraviolet light or chemical mutagens. Examples of commonly used mutagens are X-rays, ultraviolet radiation at 260 nm, N-methyl-N'-nitro-N-nitrosoguanidine, methyl-and ethylmethanesulfonic acid, sodium nitrite, sodium bisulfate, hydroxylamine, nucleic acid base analogs such as 2-aminopurine and 5-bromouracil, and acridine dyes such as proflavin. Also useful are insertlocal mutations such as insertion sequences, Mu-1 phage, or transposons such as Tn5. A *Xanthomonas campestris* strain can be exposed to one or more of these mutatens either prior to or concurrently with growth of the strain on the selection medium.

Although not all mutants capable of resisting these two antibiotics show increased xanthan production, the proportion of routants having increased xanthan production 1s sufficiently high to allow selection of strains having a xanthan-increasing modification as a result of genetic modification with relative ease. Selection for increased xanthan production can be carried out by measuring xanthan in the culture medium utilizing standard techniques, such as those exemplified in the Examples below. The selected hyperproducing strains can be either utilized as obtained or the genetic information occurring as a result of the mutation can be excised by known techniques of genetic engineering and inserted into other Xanthomonas strains for use in preparing xanthan by culturing techniques. Such genetically engineered strains containing a xanthan-increasing modification that originally arose in a different strain as a result of mutation to give either rifampicin- or bacitracin-resistance fall within the scope of the present invention. The techniques described below in both the general discussion and specific examples of genetic manipulation can be utilized to isolate the genetic information at the locus of the mutation and insert this genetic information into other strains of Xanthomonas.

The third specific technique described above for increasing xanthan production involves the use of exogenous genetic information controlling the synthesis of xanthan that has now been identified. Specific sections of Xanthomonas chromosomal DNA have been identified that control the synthesis of xanthan. FIG. 1 is a chromosome map providing restriction site information that is useful in identifying the proper sequences. Three deposits of genetic information have also been made (Apr. 10, 1987) with the American Type Culture Collection, Rockville, Md., U.S.A., under the Budapest Treaty on the International Recognition of the Deposit of Microorganisms for the Purposes of Patent Procedure. All restrictions on the three deposits will be irrevocably removed upon the issuance of a patent thereon. The three deposits are *Escherichia coli* strains containing (individually) the three genetic segments identified as C8, C9 and Cl in FIG. 1. These deposits have been accorded deposit numbers ATCC 67386, ATCC 67387, and ATCC 67388, respectively. All restrictions on the availability of the strains deposited will be revoked upon the issuance of a U.S. patent based on this application.

The genetic information from *X. campestris* can be utilized in many ways. Plasmids can be constructed containing the exogenous genetic information controlling the synthesis of xanthan, and genetic information can be introduced into an *X. campestris* host by utilizing a donor strain containing a plasmid with the desired genetic information in a triparental mating scheme to transfer the genetic information to *X. Campestris*. Suitable vectors for conjugation include a variety or plasmids displaying a broad host range. For example, IncP-group plasmids, which include RK2 and its derivatives pRK290, pLAFR1, and pRK311, and IncQ-group plasmids, which include RSF1010 and its derivative pMMb24 can be utilized. References describing these plasmids include Ditta et al., *Plasmid* (1985) 13:149–153 (plasmids RK2, pRK290, and pRK311 ); Friedman et al. , *Gene* (1982) 18:289–296 (pLAFRI); and Bagdasarian et al., *Gene* (1983)26:273–282 (pMMb24). For example, *E. coli* donor cells containing the genetic information on a plasmid, *E. coli* HB101 helper cells containing plasmid pRK2013, and recipient *X. campestris* cells can be incubated to cause genetic information transfer by conjugation. Isolation of recombinant plasmids, for example by utilization of a marker present adjacent to the genetic information being transferred, can be followed by further purification and subsequent matings. With a purified member of the original gene library to raise the frequency of exconjugates containing the exogenous genetic information.

Individual genes encoding specific peptides control factors utilized in the synthesis of xanthan can be isolated from the genetic information described above using standard techniques of recombinant DNA technology. Restriction endonucleases can be utilized to cleave the relatively large segment of genetic information containing xanthan genes into specific identifiable fragments. These fragments can be individually cloned and identified. Individual fragments can be inserted into new hosts to provide further *X. campestris* strains having increased xanthan production. Accordingly, fragments of the genetic information controlling the synthesis of xanthan also have utility in the commercial production of xanthan. The phrase "genetic information controlling the synthesis of xanthan" accordingly refers either to the original chromosomal DNA that controls xanthan synthesis as described above or fragments of this original chromosomal DNA containing one or mope individual genes capable of controlling the synthesis of xanthan (e.g., individual genes encoding an enzyme utilized in xanthan synthesis).

Specific examples showing manipulation of the genetic material are set forth in the working examples which follow. Clones containing fragments of the genetic information controlling the synthesis of xanthan have been prepared. Selection among these clones has allowed isolation of strains with improved properties, such as Increased viscosity. Genetic material has been transferred in combination with known genetic material to produce modified strains capable of being utilized in manners not previously available. For example, genetic material of the invention has been transferred alone with genetic information controlling production of lactase to provide a strain that is particularly suitable for use In preparing xanthan gum using cheese whey as a substrate.

For example, a stable recombinant strain, X59-1232, which produces quality xanthan gum from lactose, was obtained by inserting the lac genes from transposon Tn951 into the chromosome of *X. campestris* strain X59. The apparent conversion efficiency of lactose to xanthan gum by this strain was equivalent to the conversion of glucose to xanthan gum by strain X59, a strain discussed further herein which efficiently carries out the latter conversion. The viscosities of the xanthan gums from these two sources were equivalent. After more than fourteen generations of growth without positive selection for genetically linked traits, the apparent conversion efficiency from lactose by strain X59-1232 was superior to that of strain X59-pGC9114, a strain which carries the Tn951 lac genes on a multicopy plasmid (pGC9114) which, in turn, was superior to strain X59, which lacks the Tn951 lac genes. The superiority for X59-1232 could be attributed to the stable integration of the lac genes into the chromosome of X59-1232.

The apparent efficiency of conversion for clarified cheese whey to xanthan gum by X59-1232 was approximately 90% that of lactose to xanthan gum. This 10% difference from theoretical is probably within the experimental error of the measurements employed.

After a Xanthomonas strain having a xanthan-increasing modification is cultured, xanthan is separated from the culture medium utilizing any technique capable of achieving this result such as the standard techniques already being utilized commercially. See, for example, Kennedy et al., supra. and Rogovin et al., supra. One simple technique involves filtering a liquid culture medium to remove growing bacterial cells, adding isopropyl alcohol to the tiltrate to precipitate the exopolysaccharides, and collecting the precipitate on a filter followed by drying (optionally with heat and/or under a vaccuum).

The invention now being generally described, the same will be better understood by reference to the following detailed examples which are provided for purposes of illustration only and are not to be considered limiting of the invention unless so stated.

EXPERIMENTAL

Example 1

Use of Exogenous Genetic Information Controlling the Synthesis of Xanthan

In summary, mutations that block the synthesis of xanthan gum by *Xanthomonas Campestris* B1459S-4L-II were isolated as nonmucoid colonies after treatment with ethylmethane sulfonate and used to identify DNA fragments containing xanthan genes. Complete libraries of DNA fragments from wild-type *X. campestris* were cloned into *E. coli* using a broad host range cosmid vector and then transferred into each mutant strain by conjugal mating. Cloned fragments that restored xanthan gum synthesis (Xgs+; mucoidy) were characterized according to restriction pattern, DNA sequence homology and complementation of a subset of Xgs−. Groups of clones that contained overlapping homologous DNA were found to complement specific Xgs− mutations. The results suggested a possible clustering of genetic loci involved in synthesis of xanthan. Other apparently unlinked loci were also discovered. Two forms of complementation were observed. In most instances, independently isolated cosmid clones that complemented a single mutation were found to be partially homologous. Less frequent was the second form of complementation, where two cosmid clones that lack any homologous sequences restored the mucoid phenotype to a single mutant. Restoration of the wild-type mucoid phenotype was shown, in the one case that was studied in detail, to coincide with homologous recombination between a normal cloned DNA residing on a plasmid and the mutant chromosomal locus. Lastly, the degree of restoration of xanthan synthesis was measured for the complemented mutants and for wild-type *X. campestris* carrying multiple copies of the cosmid clones. Details or experiment techniques and results are set forth below.

Materials and Methods

Bacterial Strains and Plasmids

*Xanthomonas campestris* B1459S-4L-II (our strain X55) obtained from the Northern Regional Research Center was the Xgs+ (xanthan gum synthesis positive) parent of all our *X. campestris* strains. Strain X59 was a spontaneous rifampicin-resistant derivative of X55 that was also fully Xgs+. Rif$^r$ derivatives of X55 arose at a frequency of about $10^{-9}$ and were selected on agar plates containing Luria brogh supplemented with rifampicin at 60 µg/ml. Bacteriophase λb221 rex::Tn5 cI857 Oam29 Pam80 (Ruvkun et al, *Nature* (1981) 2898:85–88) was the source of Tn5 for mapping by insertional gene inactivation. Strain LE392 was the permissive host for propagating the phage. All strains and plasmids are listed in Table 1.

TABLE 1

Bacterial Strains and Plasmids

| Name | Genotype or Phenotype$^a$ | Reference or Source |
|---|---|---|
| *X. campestris* | | |
| X55 | Xgs+, prototroph | B1459S-4L-II |
| X59 | Xgs+, prototroph, Rif$^r$ | This Example |
| X59m1 | Xgs−, prototroph, Rif$^r$ | This Example |
| X59m8 | Xgs−, auxotroph, Rif$^r$ | This Example |
| X59m9 | Xgs−, prototroph, Rif$^r$ | This Example |
| X59m11 | Xgs−, auxotroph, Rif$^r$ | This Example |
| X59m31 | Xgs−, prototroph, Rif$^r$ | This Example |
| X59m45 | Xgs−, prototroph, Rif$^r$ | This Example |
| X59m48 | Xgs−, auxotroph, Rif$^r$ | This Example |
| X59m65 | Xgs−, prototroph, Rif$^r$ | This Example |
| X59m82 | Xgs−, prototroph, Rif$^r$ | This Example |
| X59m96 | Xgs−, auxotroph, Rif$^r$ | This Example |
| X59m145 | Xgs−, prototroph, Rif$^r$ | This Example |
| *E. coli* | | |
| HB101 | F− hsd20 ($r_B^-$ $m_B^-$), recA13, ara-14, proA2, lacY1, galK2, rpsL20 (streptomycin-resistance), xyl-5, mtl-1, supE44, thi, leu, λ− | Bethesda Research Labs |
| JM109 | recA1, endA1, gyrA96, thi, hsdR17, supE44, relA1, Δ(lac-proAB), [F′traD36, proAB, lacI$^q$ZΔM15] | Bethesda Research Labs |
| LE392 | F−, hsdR514, ($r_k^-$$m_k^-$), supE44, supF58, λ−, galK2, galT22, metB1, trpR55, lacY1, Δlac IZY-6 | L. Enquist |
| Bacteriophage | λb221 rex::Tn5 (Kan$^r$) cI857, Oam29, Pam80 | Ruvkun et al. Nature (1981) 289:85–88 |
| Plasmids | | |
| pRK311 | RK2 origin, Tra+, Mob−, Tet$^r$, λcos, lacZ(α) | Ditta et al. Plasmid (1985) 13:149–153 |
| pRK2013 | ColE1 origin, Imm+, Amp$^r$, Tra+, Mob+, Kan$^r$ | Figurski et al. Proc Natl Acad Sci USA (1979) 76:1648–1652 |
| pUC13 | Amp$^r$, ColE1 origin | Veira et al. Gene (1982) 19:259–268 |
| c1 | pRK311, Tet$^r$, complements m1 | This Example |
| c8 | pRK311, Tet$^r$, complements m8 | This Example |
| c8::Tn5-1→20 | Tet$^r$, Kan$^r$ | This Example |
| c9 | pRK311, Tet$^r$, complements m9 | This Example |
| c31 | pRK311, Tet$^r$, complements m31 | This Example |
| c45 | pRK311, Tet$^r$, complements m45 | This Example |

TABLE 1-continued

Bacterial Strains and Plasmids

| Name | Genotype or Phenotype[a] | Reference or Source |
|---|---|---|
| c65 | pRK311, Tet[r] complements m65 | This Example |
| c82 | pRK311, Tet[r] complements m82 | This Example |
| c1H5 | pRK311, Tet[r] complements m1 | This Example |
| c9H7 | pRK311, Tet[r] complements m9 | This Example |
| c9e | pRK311, Tet[r] complements m9 | This Example |

[a]Abbreviations: Xgs+, xanthan gum synthesis; Rif[r], rifampicin resistance; Tet[r], tetracycline resistance; Kan[r], kanamycin resistance; Amp[r], ampicillin resistance; Imm+, colicin E1 immunity; Tra and Mob, transfer and mobilization functions of RK2 plasmid.

Growth Media

Xanthomonas species were cultured by shaking in liquid YT medium at 30° C. with rifampicin at 50 μg/ml, tetracycline at 7.5 μg/ml and/or kanamycin at 50 μg/ml added for plasmid maintenance. YT medium contains Bacto tryptone (16 g/l) Bacto yeast extract (10 g/l) and NaCl (5 g/l). All nutrient agar plates contained TBAB (tryptose blood agar base from Difco) plus starch at 1% (w/v). Selection plates for conjugal matings contained tetracycline at 7.5 μg/ml, kanamycin at 50 μg/ml and rifampicin at 50 μg/ml. Minimal agar plates contained M9 inorganic salts (Anderson, Proc. Natl. Acad. Sci. USA (1946) 32:120-128) plus glucose, mannose or fructose at 1% (w/v) as the carbon source. Liquid medium for shake flask experiments to measure xanthan accumulation was referred to as "XG004" and consisted of 1X basic salts, 0.5% (w/v) tryprone, 0.25% (w/v) yeast extract, 1X trace minerals, 0.01% (w/v) CaCl and 2% (w/v) glucose. 10X basic salts consists of 6.8 g $KH_2PO_4$, 0.2 g $MgSO_4.7H_2O$, 2.2 g L-glutamlc acid, 2 g citric acid in 100 ml with pH adjusted to 7 with NaOH at 30°. C. 1000X trace minerals was 2.25 g $FeCl_3.6H_2O$ 1.41 g $MnSO_4.H_2O$, 2.2 g $ZnSO_4.7H_2O$, 0.25 g $CuSO_4.5H_2O$, 0.4 g $COCl_2.6H_2O$, 0.26 g $Na_2MoO_4.2H_2O$, 0.4 g $H_3BO_3$ and 0.06 g KI per liter of aleionized $H_2O$ (with HCl added to solubilize the salts). E. coli was grown in Luria broth at 37° C. with tetracycline at 10μg/ml and kanamycin at 50 μg/ml as appropriate or on agar plates containing Luria broth or TBAB (Difco).

Mutagenesis of X. campestris

About $2\times10^9$ freshly grown cells (an absorbance at 600 nm of 1 equals $10^9$ X. campestris cells) were suspended in 2 ml of minimal salts medium and shaken at 30° C. with 0 to 40 μl of ethylmethane sulfonate (EMS) for 1, 2 or 3 h. Samples of 0.5 ml were taken from each treatment, washed two times with YT medium and resuspended in 2 ml of YT medium and shaken overnight at 30° C. Dilutions were spread on TBAB plus 1% (w/v) starch plates. After three days, nonmucold colonies (about 1% of the total) were saved. The mutants designated X59 ml to X59m150, were tested for retention or the Rif[r] marker of the parent X59, for the presence of cleared zones around colonies on plates containing starch and for ability to utilize different carbon sources.

DNA Isolation and Recombinant DNA Techniques

Plasmid DNA was isolated by the boiling method of Birnboim and Doly (Nucleic Acids Res. ( 1979) 7:1513-1523). Frequently-used plasmids were further purified by equilibrium sedimentation in density gradients of CsCl containing ethidium bromide (Maniatis et al. 1982. Molecular Cloning, A Laboratory Manual. Cold Spring Harbor Laboratory, Cold Spring Harbor, N.Y.) . Restriction enzymes (from Boehringer Mannhelm, GmbH) were used according to the manufacturer's instructions. DNA sequence homology was demonstrated by the blotting method of Southern (Manlatis et al., supra) and used Zeta-probe (Bio-Rad) for DNA immobilization. DNA for use as a hybridization probe was labeled with [$^{32}P$]dCTP (using a nick translation reagent kit from Bethesda Research Laboratories). Fragments of DNA were separated by electrophoresis through agarose gels (0.6 to 0.7% w/v) in Tris-acetate buffer (Maniatis et al., supra) .

Conjugation and Complementation of XEs− Mutants

The complete library (or specific elements of the library) were transferred from E. coli to X. campestris by a triparental mating scheme (Ditta et al., Proc. Natl. Acad. Sci. USA (1980) 77:7347-7351 ). From fresh overnight cultures, $10^9$ recipient cells (X. campestris Xgs− mutants), $5\times10^8$ donor cells (JM109-L[X59], the library) and $5\times10^8$ helper cells (E. coli HB101 containing plasmid pRK2013) were mixed and passed through an HA 0.45 micron Millipore filter. The filters were incubated on TBAB plates overnight at 30° C. and then the cells were washed into 2 ml of selecting medium (TBAB plus tetracycline at 7.5 μg/ml and rifampicin at 50 μg/ml). The cells were diluted by $10^4$ to $10^5$ fold and spread on selection plates containing antibiotics. Complementation (restoration of the Xgs+ phenotype in an Xgs− mutant) occurred at a frequency of 0.1 to 0.5%. The Xgs+ exconjugants were purified and the recombinant plasmid was isolated and transferred back to E. coli JM109 for storage and further purification. Subsequent matings with a purified member of the library raised the Xgs+ frequency in the exconjugants to 100%.

Measurement of Xanthan Accumulation

Strains to be tested were grown in liquid XG004 medium overnight, diluted, and resuspended at the same cell density. Flasks (125 ml capacity) containing 10 ml of medium XG004 were inoculated with equal numbers of cells ($1\times10^8$) and shaken at 28° C. at 250 rpm. At the time of sampling, 20 ml of isopropyl alcohol was added to each flask to precipitate the exopolysaccharides. The precipitate was collected on a GFA filter, which was then dried in a vacuum oven, and weighed.

Results

Isolation of Mutants Deficient in Xanthan Gum Synthesis (Xgs−)

Strain X55 (NRRL B1459S-4L-II from the Northern Regional Research Center) is the "wild-type" parent of most xanthan-producing strains of X. campestris in use today. Strain X55 was the parent of all other X. campestris used in this work. A spontaneous Rif[r] derivative of X55 was isolated by spreading about $10^9$ bacteria on a plate containing rifamptein at 60 μg/ml. The Rifr phenotype of X59 was useful as a marker to distinguish progeny from contaminants following mutagenesis and as a counterselection for *E. coli* Rif$^s$ donors In conjugal matings. Both X55 and X59 form indistinguishable mucoid colonies on nutrient and minimal agar plates.

A collection of Xgs− mutants was generated by exposing strain X59 (and less frequently X55) to ethylmethane sulfonate (EMS). After growth at 30° C. for 3 d, nonmucoid colonies were selected and purified for further use. In most cases the nonmucoid colonies were distinctively different in appearance, but some independently isolated-mutants displayed similar nonmucold appearance. The latter could be distinguished by plating on different carbohydrate sources and as a function of time of growth. Only one mutant was selected from each treatment with EMS, unless colony morphology was clearly distinctive. Mutants of X59, serially designated X59ml to X59m200, were tested for the parental Rif$^r$ marker. Other indications that a survivor of mutagenesis was *X. campestris*, an amylase producer, was the clear zone surrounding colonies spread on a nutrient agar plate containing starch and the characteristic yellowish pigment of the colony. Many of the mutants were also tested for their ability to grow on minimal agar plates containing various sugar substrates in order to distinguish unique isolates from siblings.

Cloning of *X. campestris* DNA into a Cosmid Vector

Total DNA from strain X59 (Xgs+) was prepared by the boiling method of Birnbolm and Doly, supra, and partially digested with Sau3A restriction endonuclease. Large fragments of 20 to 30 kb were purified by velocity sedimentation in neutral sucrose gradients. This ensured that only contiguous chromosomal DNA fragments were inserted in 1;he cloning vector upon ligation. The cloning vector was the broad host range cosmid, pRK311 constructed by Ditta etal., Supra. DNA fragments to be cloned were inserted into the BamHI sequence of the multiple cloning site within the lacZ portion of the vector. Using the in vitro packaging kit of Stratagene, we selected for insections of DNA of about 20 to 25 kb into the cosmid vectors. The pRK311 vector also carries a selectable tetracycline-resistance gene. After in vitro ligation and packaging, *E. coli* JM109 was transfected with phage particles, and tetracycline-resistant colonies were individually saved. Each tetracycline-resistant colony contained the plasmid vector plus a 20 to 25 kb insertion of *X. campestris* DNA. A library of-fragments of DNA resulted from pooling the clones. Since the number of clones in each library exceeded 1000 we were at least 99.9% certain of having all fragments of the *X. campestris* chromosome represented at least once. Three different libraries were used in this example.

Complementation of Xgs− defects by cloned normal DNA

Intergenic conjugal matings were used to transfer DNA. The RK2-derived pRK31 I costold has a broad host range but is not self-transmissible. In order for pRK311 to be transferred by conjugation between *E. coli* and *X. campestris* a second "helper" plasmid was used, pRK2013, which has a limited host range that does not include *X. campestris*. Transfer of recombinant cosmids was accomplished by a triparental mating that included *E. coli* JM109/pRK311, JM109/pRK2013 and the recipient *X. campestris* Xgs− mutant.

About 15 different Xgs− routants were complemented and restored to mucoidy (Xgs+) by conjugal mating with the complete library or *X. campestris* genes. The frequency of complementation was about 0.1% for most matings, as would be expected if there was only one copy of each gene per chromosome. The results can be understood by considering a set of related colonies: X59-pRK311, X59m45-pRK311 and X59m45-c45. The presence of the c45 cosmid restores the mucoid appearance as seen for the wild-type X59. The mucoid phenotype for X59m45-c45 depended on the continued presence of the recombinant plasmid, as Judged by the maintenance of the $Tet^r$ gene of the plasmid. A similar overall pattern was seen for all complemented Xgs− mutants. Several mucoid exconjugants were picked and purified by replating. DNA was prepared for each and transformed into *E. coli* and then mated back into the original mutant Xgs− mutant straight. In each case this resulted in 100% complementation and all of the tetracycline-resistant exconjugants carried the same recombinant cosmid. The transformants of *E. coli* also served as a source of DNA for restriction mapping and DNA hybridization tests by Southern blotting. A summary of the complementation data is included in Table 2.

TABLE 2

Complementation of Xgs− Mutations by Wild-Type Cloned *X. campestris* DNA[a]

| | Cloned Fragment | | | | | | | |
|---|---|---|---|---|---|---|---|---|
| Mutant | c1 | c8 | c9 | c11 | c31 | c45 | c65 | c82 |
| m1 | + | ± | − | − | ± | − | ± | − |
| m8 | − | + | − | − | + | − | + | − |
| m9 | − | ± | + | + | − | − | − | + |
| m11 | − | ± | + | + | − | − | − | + |
| m31 | − | + | − | − | + | − | + | − |
| m45 | − | + | − | − | − | + | − | − |
| m48 | − | + | − | − | − | + | − | − |
| m65 | − | + | − | − | + | − | + | − |
| m82 | − | ± | + | + | ± | − | ± | + |
| m96 | − | + | − | − | + | − | + | − |
| m145 | − | − | − | NT | − | − | − | + |

[a]Xgs− mutants that received a recombinant cosmid by mating were scored for mucoid (+) or nonmucoid (−) appearance by visual inspecetion of colonies. A ± designation indicates a partial mucoidy. NT; not tested.

Alignment of Cloned Inserts and Xgs− Mutations by Restriction Mapping, DNA Hybridization and Genetic Complementation When more than one recombinant plasmid from the complete library complemented the same mutation, we usually found that they were either indistinguishable sibling clones or shared considerable DNA homology. DNA hybridization analyses demonstrated this point. Several recombinant plasmids were digested with a mixture of EeoRI and HindIII enzymes. HindIII cleaves in the multiple-cloning-site to one side of the cloned insert and EeoRI cleaves to the other side and also within the vector. This produces two fragments of vector DNA of about 8 and 13 kbp. The digestion products were separated by electrophoresis through agarose gels and two samples (A and B) containing the same gestion products were analyzed. Most of the visible bands from ethidium bromide staining were X59 DNA. The hybridization probes for the A sample were radiolabeled c45 plasmid and for the B sample, the plasmid c31. The hybridization pattern indicated that cosraids c8, c31, c45 and c65 carry overlapping segments of chromosomal DNA. The teflon in common between these four clones includes restriction fragments of 0.6 and 1.2 kb and part of the 4.3 kb fragment.

Additional hybridization results were obtained from a separate but similar analysis. Plasmid DNA was purified, restricted with a mix of EeoRI and Hind/II enzymes and fragments were separated by agarose gel electrophoresis and then transferred to filters. In a first sample the probe was radiolabeled c9H7 and in a second sample, clH5. The hybridization pattern for the first sample showed homology between c9H7, c9 and c145, but not between c9H7 and c45-2, c45-1, c8, c31, c32b, cl or clH5. The pattern of the second sample showed that clH5 is homologous only to cl. Cosmid clH5 was initially selected from the library of cloned fragments because it hybridized to cl. The hybridization results were the basis for compiling the map shown as FIG. 1.

Figure 1:
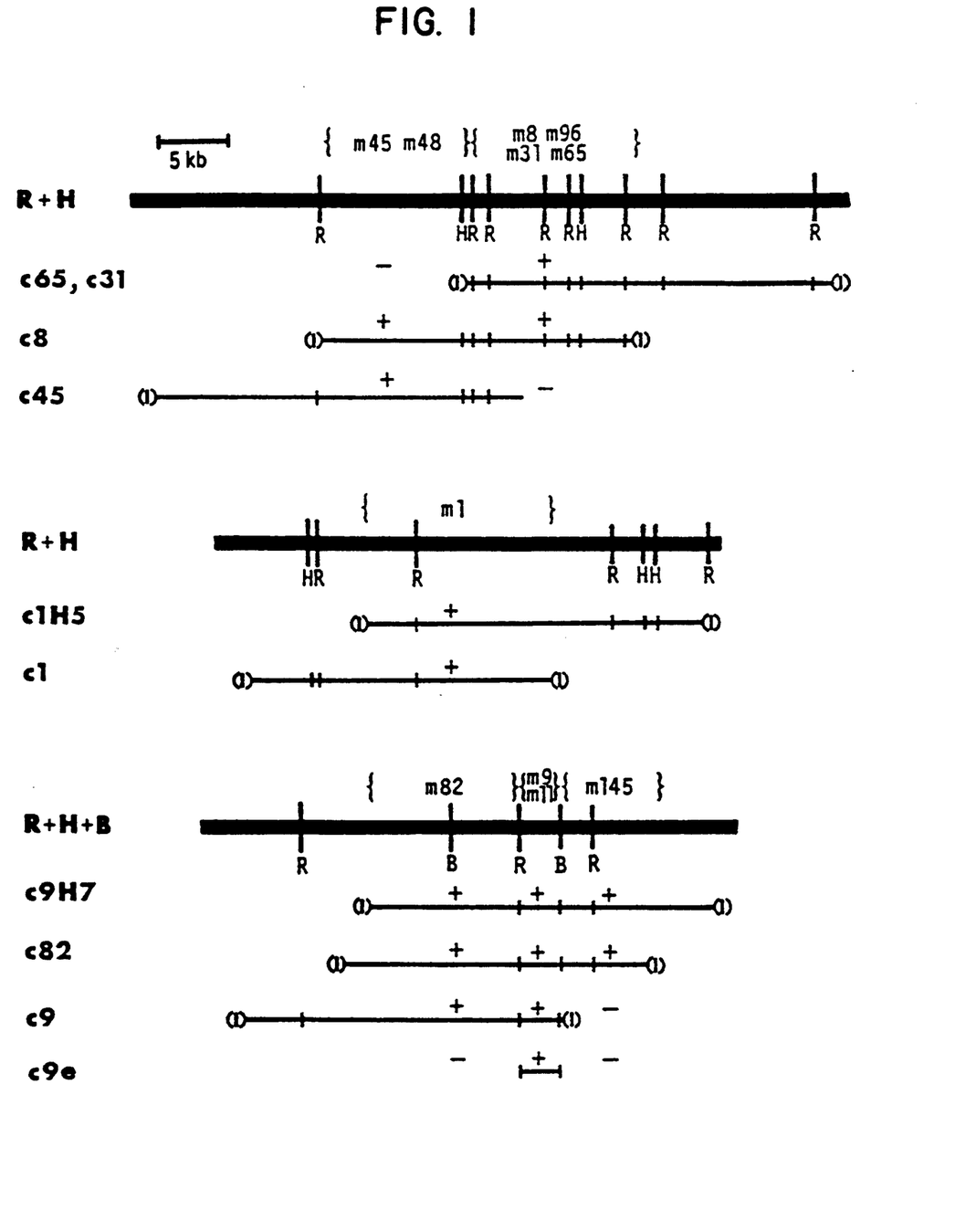
FIG. 1 is a compilation of three physical maps for *X. campestris* DNA insertions in vector pRK311 showing complementation groups. The line marked "R/H" shows the order and position or restriction cleavage sites for EcoRI and HindIII enzymes deduced from the overlapping maps obtained for individual cloned inserts. Parentheses, (), at the end of the cloned maps indicate that it was not possible to distinguish between an end generated by cleavage within the cloned insert from restriction in the adjoining multiple cloning site. The tentative map positions for Xgs− mutations are indicated above the physical maps. Unordered loci are enclosed with braces, {}.

The deduced locations of Xgs⁻ mutations are shown in FIG. 1 above the map of EcoRI and HindIII restriction sites labeled "R/H" on the left. Mutants enclosed by braces have not been ordered with respect to each other. Overlapping cloned fragments could be aligned according to restriction pattern and DNA homology. Superimposed on this alignment are the results of complementation experiments with "+" signifying restoration of the Xgs+ phenotype to an XEs⁻ mutant. The range of possible map positions for each mutant was then determined from the boundaries of each cloned fragment. Most of the mutants were distributed across a contiguous stretch of about 40 kbp, representing about 2% of the chromosome of *X. campestris*.

Two other unlinked loci involved in xanthan synthesis were also identified. One locus is represented by four overlapping cloned fragments carried on cosmids c9, cl1, c9H7 and c82. All four restore the XEs+ mucoid phenotype to the independent mutants m9, m11 and m82. Another pair of cosraids (cl and clH5) share homology with each other, but not with either of the other two sets.

Figure 2A:
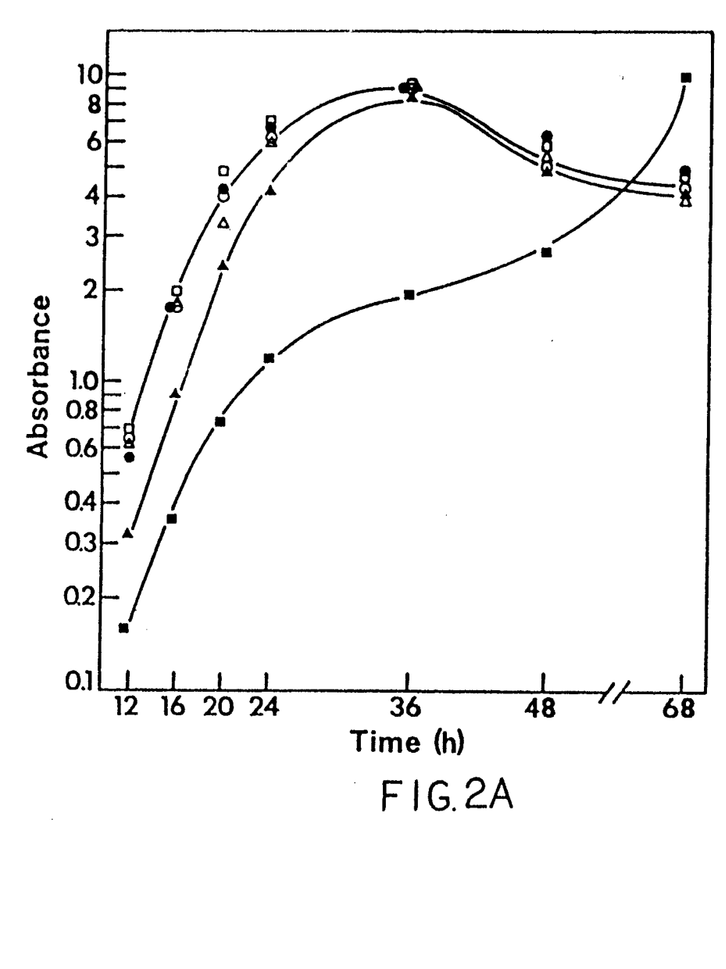
FIG. 2 is a graph showing time course of accumulation of xanthan by wild-type strain X59 carrying multiple copies of genetic information controlling the synthesis of xanthan. Recombinant plasmids containing inserts of cloned *X. campestris* DNA that restore xanthan synthesis are indicated by the following symbols: ●, X59; △, X59pRK311; ▲, X59c45; □, X59c9; ○, X59c1; ■, X59c31. Panel A shows optical density at various times of cell growth while Panel B shows xanthan accumulation. The upper curve in Panel A represents four cultures. In Panel B the solid line is for X59c45, the dashed line is for X59pRK311, and the dotted line is for X59031.
Figure 2B:
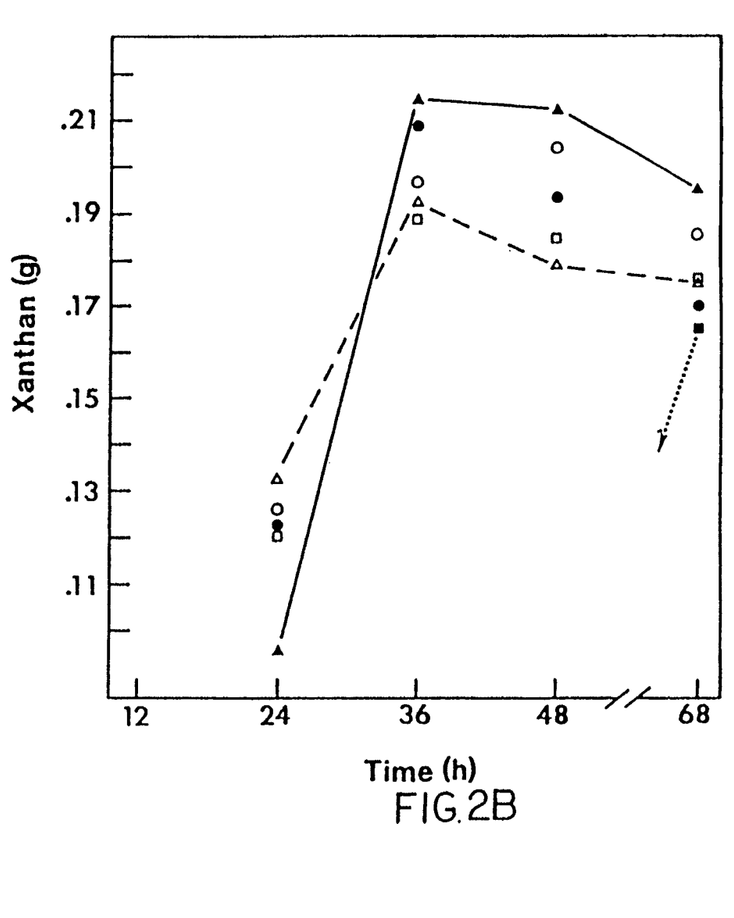

Xanthan Synthesis by Exconjugants of X59 with Multiple Copies of Complementing Cloned Genes We transferred each complementing clone by mating into X59, already XEs+, and measured xanthan synthesis. For a control we used X59 bearing the vector alone, pRK311. The cells were grown in shake flasks at 30° C., starting from inocula of 10⁷ cells per ml. The amount of xanthan was determined by standard methods: precipitation of the exopolysaccharides by two volumes of isopropanol, drying and weighing. For most complementing clones the extra gene copies had no detectable effect or caused a decrease in xanthan yield. For those that accumulated amounts of xanthan significantly higher than the control, the xanthan and cell growth data are given in FIG. 2. In no case was the increase in accumulation greater than 20%. However, the rate of xanthan accumulation between 24 and 36 hrs for X59-c45 was twice that for the control X59-pRK311. When X59 without pRK311 was included in the time course experiments we found that the large vector plasmid itself had a negative effect on xanthan synthesis (data not shown). In a similar experiment X59-c8 produced an average of 22% more xanthan gum than its parent strain X59 ( 48 -hr growth period ) .

This Example demonstrates that all of the three complementary regions described in FIG. 1 containing xanthan genes are useful in the preparation of strains showing increased xanthan production. Reproducible changes in xanthan accumulation were observed with the introduction of exogenous genetic information, but the magnitude of change was small, plus or minus about 15%. Suppression of xanthan production was caused by the large plasmid vector itself, which depressed cell growth and xanthan synthesis. Use of other plasmid vectors should improve strain productivity.

EXAMPLE 2

Subcloning of c8 Fragment and Resulting Xanthan Production

Figure 3:
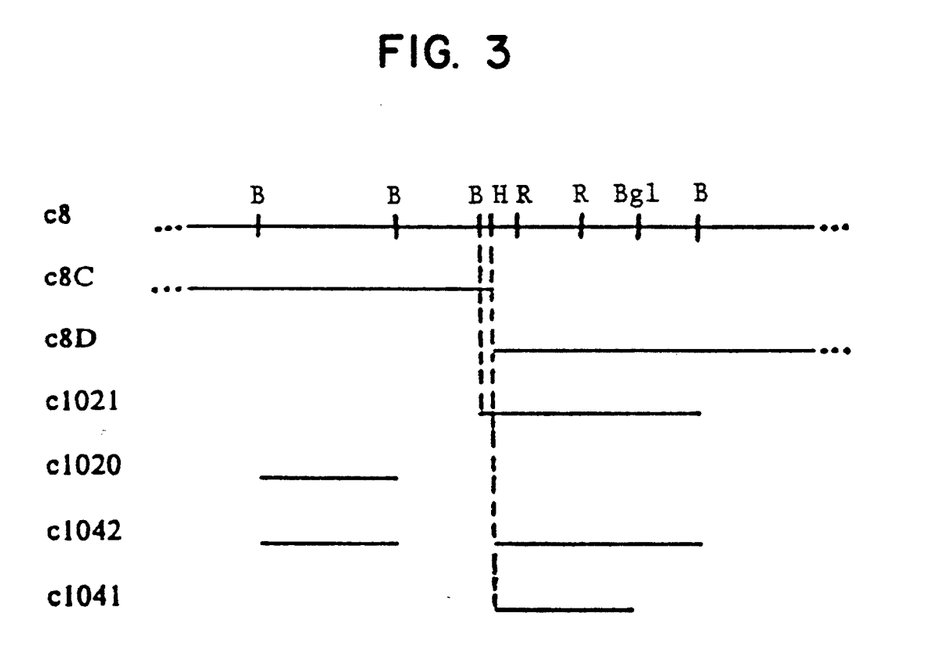
FIG. 3 is a restriction map showing subcloned fragments of the c8 fragment of *X. campestris* DNA shown in FIG. 1. Abbreviations: B, BamHI; Bgl, BglII; H, HindIII; R, EcoRI.

The "c8" fragment of *X. campestris* DNA was further subcloned to localize the beneficial genetic traits. The subcloned portions are diagrammed in FIG. 3, relative to c8 as given in FIG. 1.

Each subclone was inserted in the vector used for most of this work, pRK311, and transformed first into *E. coli* and then conjugally mated from *E. coli* to *X. campestris* strains X55, X59 and X50. Cell growth and xanthan accumulation were measured in 100-500 ml shake flasks with nutrient medium containing per liter of tap water: 10 g peptone, 20 g glucose., 3.5 g $K_2HPO_4$, 2.6 g $KH_2PO_4$, 0.26 g $MgSO_4.7H_2O$, 6 mg $H_3BO_3$, 6 mg ZnO, 2.6 mg $FeCl_3.6H_2$), 20 mg $CaCO_3$ and 0.13 ml 11.6 N HCl. Viscosities for crude culture broths and semi-purified xanthan gum were determined. As in Example 1, partial purification of xanthan was by precipitation of polysaccharide by addition of two volumes of isopropyl alcohol and collection of the precipitation on a GFA filter followed by drying and weighing. The results are tabulated below:

TABLE 3

| | | | Viscosity (cps at 1 rpm)[a] | |
|---|---|---|---|---|
| Host | Plasmid | Yield (g xanthan/l) | Fermentation Broth | 0.5% (w/v) Semi-purified Xanthan |
| X59 | pRK311 | 14 | 620 | 340 |
| | c8 | 17 | 1000 | 300 |
| | c8C | 15 | 1300 | 480 |
| | c8D | 14 | 420 | 110 |
| | c1021 | — | — | — |
| | c1020 | 12 | 140 | 270 |
| | c1042 | 17 | 500 | 170 |
| | c1041 | 17 | 710 | 320 |
| X50 | pRK311 | 16 | 1700 | 420 |
| | c8 | 17 | 2100 | 460 |
| | c8C | 17 | 3200 | 800 |
| | c8D | 14 | 930 | 290 |
| | c1021 | 13 | 880 | 320 |
| | c1020 | 15 | 420 | 300 |
| | c1042 | 18 | 960 | 270 |

[a]Brookfield LV viscometer with spindle number 18 or 31. Fermentation broths were diluted 1:1 with 0.1 M NaCl prior to measuring viscosities.

Subclone c8c accumulates as much xanthan in the culture broth as the parent clone C8; however, the product has an unexpected higher viscosity per weight of semi-pure material. Thus, the cloning and reintroduction of cloned DNA into *X. campestris* affects both quantity and quality of xanthan, and improved viscosity (or other properties) can be obtained routinely by selecting subclones having the desired property.

EXAMPLE 3

Drug-Resistance and Xanthan Synthesis

Two different mutant phenotypes were associated with elevated accumulation of xanthan gum by *Xanthomonas campestris* (strain B1459). Among a set of spontaneous rifampicin-resistant mutants of the above strain (designated "X55" in this collection: see Example 1 above), there is a subset that accumulates more xanthan gum in the growth medium. The rifampicin-resistant derivatives that show this unexpected phenotype were X59, X34, X37 and X44. As shown in Table 4, these strains accumulate more xanthan compared to the rifampicin-sensitive parent X55.

A second phenotype, bacitracin-resistance, is also associated with elevated xanthan synthesis. Strain X50 is a bacitracin-resistant derivative of the rifampicin-resistant X59. The double mutant accumulates more xanthan gum than either its parent X59 or X55.

TABLE 4

Synthesis of Xanthan Gum by Antibiotic-Resistant *X. campestris*

| Phenotype | Strain[a] | 1 | 2[c] | 3[c] | 4 | 5[c] | 6[c] | 7[c] | 8 | 9 |
|---|---|---|---|---|---|---|---|---|---|---|
| Rif[s] | X55 | 37 |  | 38 | 32 | 27 | 119 | 159 |  |  |
|  |  | 41 |  |  |  |  |  |  |  |  |
| Rif[r] | X59* | 45 | 46 | 36 | 36 | 147 | 199 | 177 | 181 |  |
|  |  | 46 |  |  |  |  |  |  |  |  |
| X30 |  | 39 |  |  |  |  |  |  |  |  |
| X31 |  | 41 |  |  |  |  |  |  |  |  |
| X32 |  | 40 |  |  |  |  |  |  |  |  |
| X33 |  | 39 |  |  |  |  |  |  |  |  |
|  |  | 39 |  |  |  |  |  |  |  |  |
| X34* |  | 45 |  |  |  | 149 | 180 |  |  |  |
|  |  | 43 |  |  |  |  |  |  |  |  |
| X35 |  | 40 |  |  |  |  |  |  |  |  |
| X36 |  | 39 |  |  |  |  |  |  |  |  |
| X37* |  | 51 |  |  |  | 143 | 186 |  |  |  |
|  |  | 44 |  |  |  |  |  |  |  |  |
| X38 |  | 39 |  |  |  |  |  |  |  |  |
| X39 |  |  |  | 29 |  |  |  |  |  |  |
| X40 |  |  |  | 30 |  |  |  |  |  |  |
| X41 |  |  |  | 29 |  |  |  |  |  |  |
| X42 |  |  |  | 30 |  |  |  |  |  |  |
| X43 |  |  |  | 30 |  |  |  |  |  |  |
| X44* |  |  |  | 33 | 36 | 153 | 196 |  |  |  |
| X45 |  |  |  | 29 |  |  |  |  |  |  |
| X46 |  |  |  | 29 |  |  |  |  |  |  |
| X47 |  |  |  | 31 |  |  |  |  |  |  |
| X48 |  |  |  | 30 |  |  |  |  |  |  |
| X49 |  |  |  | 34 | 29 |  |  |  |  |  |
| RM108* |  |  |  |  |  |  |  |  | 182 |  |
| RM102* |  |  |  |  |  |  |  |  | 179 |  |
| RM109 |  |  |  |  |  |  |  |  | 158 |  |
| RM101 |  |  |  |  |  |  |  |  | 157 |  |
| Rif[r]Baci[r] | X50* |  |  |  |  | 41 |  |  | 195 | 192 |

[a]The values in the table are mg of dried precipitate per sample. Strains X30 through X49 were consecutively numbered, random, rifampicin-resistant derivatives of X55. RM108, 102, 109 and 101 were not random isolates. Each overproducer is marked by an asterisk.
[b]For experiments 1–5, the sample size was 8 g of culture broth; for experiments 6–9, the sample size was 10 g. The polysaccharides were precipitated from the sample by adding 2 volumes isopropyl alcohol and mixing. The precipitate was collected by filtration onto a 2.5 cm Whatman 934-AH glass fiber filter and then dried in a vacuum at 80° C. and weighed. Culture samples were harvested at 48 hours. The cultures were 20 ml in 250 ml triple-baffled Erlenmeyer flasks. The growth medium for experiment 2 was (per liter of tap water): 1 g $(NH_4)_2HPO_4$, 1 g $NaNO_3$, 1 g Amberex, 0.01 g $MgSO_4.7H_2O$, 0.1 g $CaCl_2$, 20 g glucose and 1X trace minerals. For experiments 1, 3, 4 and 5 the medium was (per liter of tap water): 3 g yeast extract, 3 g malt extract, 5 g peptone and 20 g glucose. For experiments 6 and 7 the medium was (per liter of tap water): 5 g tryptone, 2.5 g yeast extract, 6.8 g $KH_2PO_4$, 0.2 g $MgSO_4.7H_2O$, 2.2 g glutamic acid, 2 g citric acid, 0.1 g $CaCl_2$, 20 g glucose and 1X trace minerals. 1000X trace minerals were (per liter of deionized water) 2.25 g $FeCl_3.6H_2O$, 1.41 g $MnSO_4.H_2O$, 2.2 g $ZnSO_4.7H_2O$, 0.25 g $CuSO_4.5H_2O$, 0.4 g $CoCl_2.6H_2O$, 0.26 g $Na_2MoO_4.2H_2O$, 0.4 g $H_3BO_3$ and 0.06 g KI. The medium for experiments 8 and 9 was (per liter of tap water): 10 g peptone, 20 g glucose, 3.5 g $K_2HPO_4$, 2.6 g $KH_2PO_4$, 0.26 g $MgSO_4.7H_2O$, 6 mg $H_3BO_3$, 6 mg ZnO, 2.6 mg $FeCl_3.6H_2O$, 20 mg $CaCO_3$ and 0.13 ml 11.6 N HCl.
[c]Average values from two independent flasks.

The techniques utilized to obtain these resistant strains are described below.

Rifampicin

At least $10^9$ bacteria of strain X55 were spread on plates (YM plus glucose) containing rifampicin at 50–100 μg/ml, usually 60 μg/ml. The cultures were incubated at 30° C. for 2–3 days. The colonies that appeared were inspected. Colonies that appeared mucoid (Xgs+) and resistant to rifampicin upon restreaking to purify the mutated derivative were tested for accumulation of xanthan as described in the legend to Table 4 above.

Bacitracin

To isolate bacitracin-resistance strains, either X55 or the rifampicin-resistant derivative X59 was utilized. The results given in this example are for X59. About $10^9$ bacteria of strain X59 were spread evenly on plates (YM plus glucose) and allowed to dry. Then a drop of a solution containing bacitracin at 1–5 μg/ml water was spotted on the center of the plate. After 1–2 days of growth at 30° C., a clear zone was present where the bacitracin was added. Just inside the boundary separating the no-growth region from the growth region were several small colonies that survived the antibiotic treatment. These were picked and restreaked on plates (YM plus glucose) containing bacitracin at a concentration of 0.5 mg/ml.

Derivative X50 was obtained from parent X59. Other bacitracin-resistant colonies were seen but were not xanthan producers; such non-mucoid colonies were not studied further.

EXAMPLE 4

Fermentation Conditions

Fermentor inocula were prepared in two growth steps. Four agar plates containing Luria broth were each spread with a loopful of concentrated cells that were stored frozen at −70° C. in 15% (v/v) glycerol. When the plates reached confluency (about 48 hrs at 30° C.), the cells were harvested by scraping and divided between two 2 l flasks containing 500 ml of Luria broth. The flasks were incubated at 30° C. with vigorous shaking for about 16 hrs to yield 10% (v/v) inocula for each strain.

The aerobic "fermentations" were conducted in a Braun Biostat E fermentor using 10 l of the 15 l capacity in either batch or fed-batch mode. The vessel was 430 mm high and 203 mm in diameter and the liquid height was 343 mm. There were 4 Rushton turbine impellets, each with 6 flat blades. For batch fermentation the non-optimized medium contained (per liter of tap water): 50 g (glucose equivalents) corn syrup (CPC or Hubinger), 1 g Amberex 510 (Universal Foods Corp.), 1 g $(NH_4)_2HPO_4$, 1 E $NaNO_3$, 0.1 g $CaCl_2$, 0.01 g $MESO_4.7H_2O$ and 1 ml 1000X trace elements. The latter is comprised of (per liter of aleionized water): 2.25 E $FeCl_3.6H_2O$, 2.2 g $ZnSO_4.7H_2O$, 1.41 E $MnSO_4.H_2O$, 0.4 E $COCl_2.6H_2O$, 0.4 g $H_3BO_3$, 0.26 $Na_2MoO_4.2H_2O$, 0.25 g $CuSO_4.5H_2O$ and 0.06 g KI. The pH was maintained at 7 by incremental addition of 2.5 N NaOH or 0.5 N HCl. Dissolved oxygen was regulated at 60% by air flow variation from 0.5–20 l/min and agitation speeds between 300 and 1000 rpm. The fed-batch fermentations were as above, but with these changes. The medium consisted of the following per liter of tap water: 15 g peptone or yeast extract, 3.5 g $K_2HPO_4$, 2.6 g $KH_2PO_4$, 0.26 g $MgSO_4.7H_2O$, 6 mg $H_3BO_3$, 6 mg ZnO, 2.6 mg $FeCl_3.6H_2O$ and 20 mg $CaCO_3$. The pH was adjusted to 7.0 with 2.5 N NaOH. The feeding medium was the same but without the peptone and was 6X concentrated. The feed was pumped into the vessel at a rate of 60–100 ml/hr.

Analytical Procedures

Figure 4:
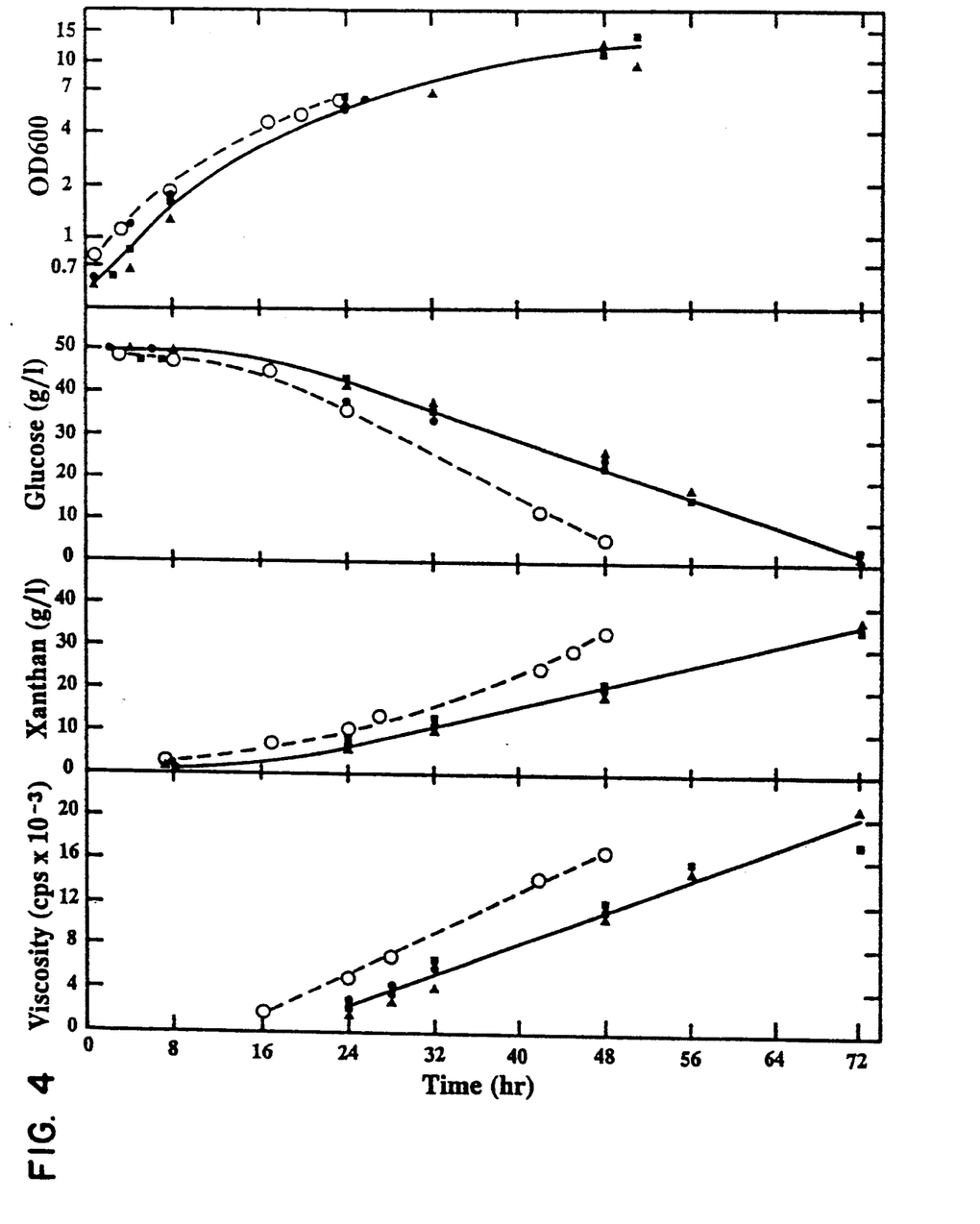
FIG. 4 is a graph with four panels showing four different characteristics of three control cultures in comparison to a rifampicin-resistant strain, X59.
Figure 5:
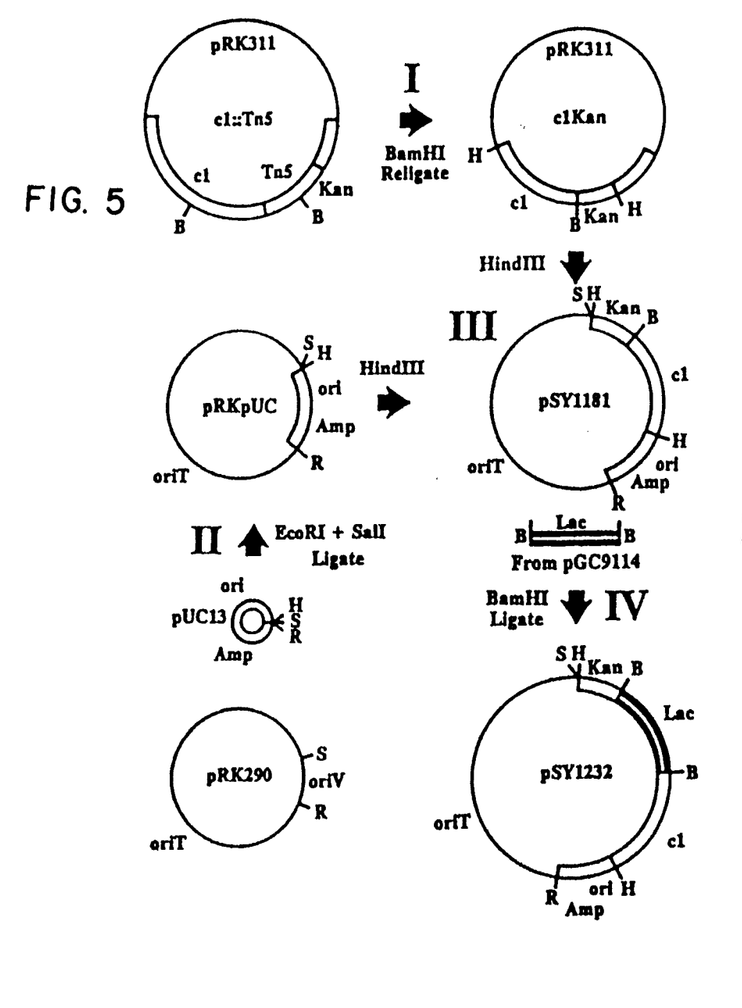
FIG. 5 is a schematic diagram showing construction of a Lac+ integration vector. The circular genetic maps are drawn roughly to scale. Plasmid pSY1181 is a general purpose integration vector and carries a DNA segment (cI) that is identical to an *X. campestris* chromosomal sequence. Plasmid pSY1232 carries in addition the lac genes from Tn951.

The amount of xanthan accumulated in the growth medium was determined by weighing a sample of about 10 ml and precipitating the polysaccharides with two volumes of isopropyl alcohol. The precipitate was collected on a glass filter (Whatman 934-AH), dried in a vacuum at 80° C. and weighed. For viscosity measurements the dried precipitate was ground in a mortar and sieved through a 250 micron mesh before resuspending in a 0.1% (w/v) NaCL. Viscosity measurements over a range of shear rates at room temperature were made with a Brookfield LVT viscometer. Protein concentrations were determined with the "BioRad Protein Assay" and standards of bovine serum albumin (Sigma)-Fermentation Fermentation of Mutants of *X. campestris* at the 10 1 Scale Two modes of fermentation were carried out: batch and fed-batch. We did not rigorously optimize the culture conditions for either mode. The batch mode conditions were adopted from several reports in the literature. The results of four fermentations are given in FIG. 4. Three control cultures (X55, ●; X56, ▲; X57, ■) were compared to the rifampicin-resistant X59, 0. Strains X56 and X57 are *X. campestris* NRRL-B1459 obtained from the Northern Regional Research Center and the American Type Culture Collection (ATCC 13951), respectively. As shown in the four panels in FIG. 4, the three controls were not distinguishable for cell density, glucose consumed, xanthan produced or culture viscosity. The mutant strain, X59, was different in three respects. First, the rate of consumption of glucose is 1.4 times faster for X59 for the time interval beginning at about 20 hrs and extending until the end of the fermantation. Second, for this interval, xanthan accumulation is about 1.5 times higher for X59Third, the viscosity of the X59 fermentation broth is about 1.6 times higher than the three controls. These three differences are of similar magnitudes. We believe that the improvement in productivity for strain X59 reflects a more efficient conversion of the substrate glucose to xanthan gum rather an effect on cell growth rates or final cell mass.

The two strains X59 and X50 were also grown in fed-batch mode with an improved medium. Modifications of conditions were initially tested at the shake flask level. The results of the fed-batch fermentations are summarized in Table 5. The nitrogen source was either yeast extract or peptone (casein). Feeding was with a glucose plus salts solution such that glucose averaged about 25 g/l, but ended at about 5-10 g/l. As seen earlier in shake flask experiments, the bacitracin-resistant derivative of X59 accumulated more xanthan than its parent. No attempt was made to optimize the culture conditions for strain X50.

TABLE 5

Fed-batch Fermentations

| Strain: | X59 | | | | X50 | |
|---|---|---|---|---|---|---|
| Medium: | Yeast Extract | | Peptone | | Peptone | |
| Hours: | 48 | 61 | 48 | 63 | 48 | 71 |
| Absorbance (600 nm) | 11 | 12 | 17 | 15 | 15 | 15 |
| Xanthan (g/l) | 47 | 59 | 49 | 58 | 52 | 66 |
| Viscosity (cps × $10^{-3}$) | 27 | 38 | 37 | 47 | 33 | 45 |
| Yield (g xanthan/g glucose) | — | 0.80 | — | 0.85 | — | 0.85 |
| Global productivity (g xanthan/1/h) | 0.98 | 0.96 | 1.04 | 0.92 | 1.07 | 0.92 |

EXAMPLE 5

Direct Utilization of Lactose in Clarified Cheese Whey for Xanthan Gum Synthesis In this example we describe the construction of a plasmid vector that is useful for integrating foreign DNA into the chromosome of *X. campestris*. Using this vector we inserted the lac genes from pGC9114 (RP1 ::Tn951) into a rifampicin-resistant derivative of *X. campestris* B1459. The genetic stability of lactose utilization and conversion of lactose or lactose in clarified whey to xanthan gum was determined. In addition, a preliminary characterization of the quality of the xanthan gum made by this strain from clarified cheese whey is described.

Materials and Methods

Bacterial Strains, Plasmids and Growth Conditions

Some materials are described in Example 1. *X. campestris* B1459S-4L-II (our strain X55) was obtained from the Northern Regional Research Center in Peoria, Ill. *E. coli* strain MC1009 (Δlac. ipozy-X74, galK, galU, Δara-leu-7697, strA, recA) was obtained from J. Hoch and strain JC3272 (his, trp, lys, Δlac ipozy-X74, strA) containing plasmid pGC9114 (RP1::Tn951 ) from G. Somkutl. Plasmid pRK290 was obtained from D. Helinskl (Ditta etal., *Proc. Natl. Acad. Sci. USA* (1980) 77:7347-7351 ) . Xanthomonas strains were cultured at 30° C. in four related liquid or solid (with agar) media: YT (10 g/l Difco yeast extract, 16 g/l Difco tryprone, 5 g/l NaCl); YTS (5 g/l Difco yeast extract, 5 g/l Difeo tryptone, 3.5 g/l $K_2HPO_4$, 2.6 g/l $KH_2PO_4$, 0.26 g/l $MESO_4.7H_2O$, 6 mg/l $H_3BO_3$, 6 mg/l ZnO, 2.6 mg/l $FeCl_3.6H_2O$, 20 mg/l $CaCO_3$); YPS (with an equal weight of peptone substituted for tryptone in YTS); PS (10 g/l peptone substituted for yeast extract and tryptone in YTS); S (2 to 4 g/l $[NH_4]_2SO_4$ substituted for yeast extract and tryprone in YTS). The volume of culture was always one-tenth to one-fifth the flask capacity. *E. coli* strains were grown in LB broth or YT. Antibiotics and carbohydrate were added as needed. They was "sweet whey" from Sigma. It was 65% lactose by dry weight, 13% protein, 8% ash and 2% lactic acid- A 30% (w/v) solution was autoclave at 121° C. for 20 rain and centrifuged to clarify. The pH before autoclaving and after clarification was about 6. The phenol-$H_2SO_4$ assay was used to measure final lactose concentration.

DNA Preparation and Analysis

See Maniartis et al., *Molecular Cloning: A Laboratory Manual* (1982) Cold Spring Harbor Laboratory, Cold Spring Harbor, N.Y., for standard cloning techniques. DNA was prepared by the boiling method or the Birnboim and Doly procedure (*Nucleic Acids Res.* (1979) 1:1513-1523) and when necessary purified by equilibrium sedimentation in density gradients of CsC1 containing ethidium bromide. Restriction enzymes and DNA ligase were used according to the instructions of the manufacturer. Transformation of *E. coli* cells with plasmids or ligation mixtures was standard and conjugal transfer of plasmids into *X. campestris* follows the triparental mating scheme (Ditta et al., *Proc. Natl. Acad. Sci. USA* (1980) 77:7347-7351 ).

Xanthan Gum Isolation and Analysis

In order to measure amounts of xanthan gum, culture samples (without prior removal of cells) were added to two volumes of isopropyl alcohol. The precipitated material was collected by filtration onto Whatman 934-AH filters, then dried at 80° C. in a vacuum oven and weighed. For viscosity measurements the dried precipitate was ground in a mortar and sieved through a 250 micron mesh before resuspending in 0.1% (w/v) NaCl. Viscosity measurements over a range of shear rates at room temperature were made with a Brookfield LVT viscometer. Protein concentrations were determined with the BioRad Protein Assay and standards of bovine serum albumin (Sigma).

RESULTS

Construction of Lactose-Positive *X. campestris*

Plasmid pGC9114 is a derivative of plasmid RP1 and carries Tn951, a transposon that confers lactose-utilization. We verified that a subfragment of pGC9114 of about 10.5 kbp and flanked by BamHI restriction sites carried the lac genes. We subcloned that fragment to pUC13 and transformed Lac⁻ *E. coli* MC1009 to Lac⁺(blue colonies on nutrient plates containing XgaI and IPTG). The same 10.5 kbp fragment was subcloned into a plasmid "integration" vector (pSY1181) that could be conjugally transferred from *E. coli* to *X. campestria* but could not replicate in the latter. We call this an "integration" vector since the only way that the lac genes can be stably maintained in the recipient is if they recombine with and become integrated into the bacterial chromosome. The four steps in the construction of plasmids pSY1181 and pSY1232 are diagrammed in FIG. 5 and explained below.

To promote integration into the chromosome we included a fragment of chromosomal DNA in pSY1232. Isolated fragments of the *X. campestris* wild-type chromosome that complemented or restored xanthan gum synthesis to mutants unable to make the polysaccharide are described in Example 1. Colonies of both the wild-type and mutants carrying the "xanthan" genes cloned on cosmid vectors were mucold, while the routants alone were nonimucoid. One such clone was cl, a recombinant between the cosmid vector pRK311 and an approximately 22 kbp chromoactual fragment. A derivative of cl, which carried transposon Tn5 (kanamyein-resistance) in a site within cl but which did not inactivate complementation by cl for the corresponding mutant ml, was our starting material. As shown by Step 1 of FIG. 5, this plasmid was restricted with BamHI enzyme and recircularized to create a single BamHI cloning site flanked by the cl complementing DNA and the kanamycin-resistance gene of TnS. The cl-Kan region is bounded by HindIII sites.

The second step was to convert the matable broad host range plasmid pRK290 to narrow host range by substituting the origin of replication from pUC13 for the oriV of pRK290. The third step was to fuse cl-Kan with pRKpUC via the HindIII sites to create the "integration" vector pSY1181. The last step was to insert the lac genes at the BamHI site of pSY1181 to generate pSY1232. *E. coli* MC1009 transformed with pSY1232 are resistant to ampicillin and kanamyein and give blue colonies on plates containing Xgal and IPTG.

In order to allow *X. campestris* to utilize lactose we transferred pSY1232 into strain X59 using a triparental conjugation scheme with pRK2013 as the helper plasmid (Ditta et al. , op. cit.) . Exconjugants were initially selected on kanamycin since *X. campestris* is naturally resistant to ampicillin, the other resistance gene carried on pSY1232. All the $Kan^R$ exconjugants were then shown to grow on minimal plates with lactose, unlike X59. The $Kan^R$ Lae+ exconjugants were indistinguishable, and one, named X59-1232, was chosen as representative for further work. Similar results were obtained by mobilizing the Lac+ plasmid pGC9114 into X59. In liquid cultures we found that the plasmid-bearing X59-pGC9114 grew more slowly than either X59 or X59-1232, which grew at similar rates. We tentatively attributed this slower growth to the "cost" of maintaining the multi-copy plasmid.

We immediately noticed that in the absence of tetracycline selection the plasmid pGC9114 was lost from a culture of X59, whereas in the absence of kanamycin selection for strain X59-1232 the cryptic marker was retained. More importantly the ability to utilize lactose behaved in the same way. This was consistent with there being at least part of the pSY1232 DNA stably integrated in the bacterial chromosome. By DNA hybridization analysis, we confirmed that the narrow host range plasmid had integrated into the chromosome (data not shown). Furthermore, the restriction fragment sizes were consistent with insertion into the chromosomal region. Similarly, the vector pSY1181 also integrates in this region, so that the strain becomes resistant to kanamycin.

Stability of Integrated Lactose Genes

Since the overall objective was to generate a stable strain fop converting lactose to xanthan gum, we measured stability for this trait after serially subculturing X59-pGC9114 and X59-1232 for many generations without tetracycline for selection of plasmid pGC9114 or kanamycin in the case of X59-1232. In either case, the X59 host is resistant to rifampicin. This allows a counterselection for rifampicin-sensitive accidental contamination during repeated serial transfer. Each strain was grown both in glucose and lactose, and the ratio of the amount of xanthan produced from lactose to glucose was calculated. The results are given in Table 6. The ability to convert lactose to xanthan gum by the plasmid bearing strain, X5 9pGC9114, decreased to half its original level at the third passage. In contrast, X59-1232 carrying the lac genes integrated into the chromosome showed stable conversion of lactose to xanthan gum through the end of the parallel experiment, a total of 42 generations.

TABLE 6

Genetic Stability of Utilization of Lactose for Xanthan Gum Synthesis

| Passage Number[a] | Generation Number[b] | Xanthan Gum (weight percent) X59pGC9114 Lac | Glc | Lac/Glc | X59-1232 Lac | Glc | Lac/Glc |
|---|---|---|---|---|---|---|---|
| 0 | 7 | 1.6 | 2.0 | 0.8 | 1.6 | 1.9 | 0.8 |
| 1 | 14 | 1.7 | 2.0 | 0.9 | 1.7 | 2.0 | 0.9 |
| 3 | 28 | 0.6 | 1.5 | 0.4 | 1.5 | 1.7 | 0.9 |
| 4 | 35 | 0.1 | 1.8 | 0.1 | 1.5 | 2.0 | 0.8 |
| 5 | 42 | 0.2 | 1.7 | 0.1 | 1.7 | 2.2 | 0.8 |

[a]Initial inocula were grown in YT plus rifampicin (50 μg/ml) with tetracycline (7.5 μg/ml) for X59pGC9114 or kanamycin (50 μg/ml) for X59-1232. Each passage was in YT plus rifampicin with an inoculum of $10^7$ cells/ml and was ended at about $10^9$ cells/ml (O.D. 600 = 1). After each passage, shake flasks YPS medium with either lactose or glucose at 2% (w/v) were inoculated with $10^7$ cell/ml. After 48 hrs the amount of xanthan gum in each flask was measured by precipitation with 2 volumes of isopropyl alcohol and then dried and weighed.

[b]Includes about 7 generations per passage and about 7 generations during carbohydrate conversion assay.

Utilization of Carbohydrate Substrate for Xanthan Gum Synthesis

Parallel shake flask cultures of strains X59 (Lac$^-$) and X59-1232 (Lac$^+$) were tested for utilization of carbohydrate for the synthesis of xanthan gum. Exopolysaccharide accumulation was measured with glucose, lactose and clarified cheese whey at equivalent weight percents of glucose or lactose. The results are given in Table 7. The Lac$^-$ parental strain X59 did not convert appreciable lactose or lactose in clarified whey to xanthan gum, compared to the stable Lac$^+$ strain X59-1232. Since the residual amounts of substrates from the carbohydrate, yeast extract, tryprone and whey were not determined, we could not calculate the absolute conversion efficiencies. However, the amounts of xanthan gum shown in Table 7 are similar to those of our most productive strains of *X. campestris*, which can convert over 70% of-substrate to xanthan during controlled fermentations.

TABLE 7

Utilization of Carbohydrate Substrate for Xanthan Gum Synthesis

| Strain | Carbohydrate Substrate | Xanthan Gum (weight percent)$^a$ 12 Hrs | 24 Hrs |
|---|---|---|---|
| X59 (Lac$^-$) | glucose | 1.2 | 2.1 |
|  | lactose | 0.2 | 0.2 |
|  | whey lactose | 0.0 | 0.4 |
| X59-1232 | glucose | 1.1 | 2.0 |
| (Lac$^+$) | lactose | 1.6 | 2.0 |
|  | whey lactose | 1.7 | 1.8 |

$^a$Inocula were grown in YT medium with rifampicin (50 μg/ml), centrifuged, washed with LB broth and resuspended at 2 × 10$^9$ cells/ml in YTS medium plus carbohydrate substrate at 2% (w/v). Samples were withdrawn and xanthan was precipitated with 2 volumes of isopropyl alcohol, and then dried and weighed.

Figure 6:
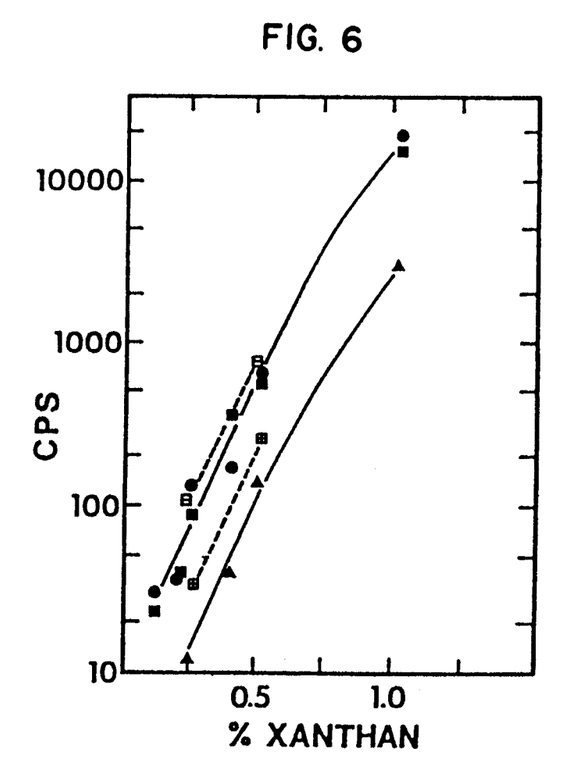
FIG. 6 is a graph showing viscosity of xanthan-containing material made from glucose, lactose, or clarified whey. Solutions of xanthan gum were prepared at defined concentrations and to the exclusion of water, ash, and protein. Viscosities at different shear rates were measured, and the values from a shear rate of 1.32 sec$^{-1}$ were plotted. Symbols, strains and growth or processing conditions: ●, X59 (Lac−), glucose; ■, X59-1232 (Lac+), lactose; ▲, X59-1232 (Lac+), clarified whey; ⊟, X59-1232 (Lac+), lactose, without clarified whey added at harvest; ⊞, X59-1232 (Lac+), lactose, with clarified whey added at time of harvest.

Quality of Xanthan Gum Produced from Glucose, Lactose and Clarified Cheese Whey The following cultures were grown in shake flasks containing 200 ml of PS medium supplemented with the indicated carbohydrate at 2% (w/v): strain X59, glucose; X59-1232, lactose: X59-1232, clarified cheese whey (lactose). After 48 hrs growth the culture contents were precipitated with 2 volumes of isopropyl alcohol, dried and ground to uniform particle size (about 100-200 microns). Samples of each were resuspended in 0.1% (w/v) NaCl at specific weight percentages, with the weights determined to the exclusion of water, protein and ash. Viscosities were measured over a range of shear rates and the results are given in FIG. 6. The solution viscosities for the xanthan-containing material made by X59 from glucose or X59-1232 from lactose were not distinguishable. However, the material made in the presence of clarified cheese whey appeared to be less viscous, requiring almost twice as much by weight to give equal viscosity. A subsequent mixing experiment indicated that an unknown clarified whey component lowers the viscosity of xanthan gum. We prepared a separate culture of X59-1232 grown on PS medium plus lactose. The xanthan-containing material was precipitated either in the presence or absence of added clarified whey. Enough clarified whey was added to make the final lactose concentration 2% (w/v). The resulting viscosities from this mixing experiment are superimposed on FIG. 6. Most of the apparent qualitative difference is accounted for by the whey effect on viscosity.

EXAMPLE 6

Mutant Selected for Two Growth Stages

One mutant (m9, used to identify the c9 genes as described in Example 1) is non-mucoid on Luria broth plates, which lack glucose. However, we later found that it is mucoid if glucose is present in the culture medium. Growth studies at the shake flask level (see Tables 8 and 9) indicate that it is a more productive strain than X59, which in turn is better than the starting strain X55. Using recombinant DNA methods and cloned DNA that complements the m9 defect, we created an apparent deletion in the m9 chromosomal region by first making a deletion in the cloned c9 DNA and then recombining the modified DNA into the X50 chromosome. The results are tabulated below in Table 9. This mutant m9 should be particularly useful in a two-part fermentation, where we emphasize cell growth rate initially and then switch conditions to emphasize xanthan synthesis. Mutant m9 grows at least as fast as wild-type in medium lacking glucose and also makes more xanthan than wild-type.

TABLE 8

| Growth Condition | % (w/v) Xanthan in Flask | |
|---|---|---|
|  | X59 | X59m9 |
| Medium lacking glucose | 0.13 | 0.0 |
| Medium with 2% (w/v) glucose | 1.6 | 1.7 |
| Medium with 2% (w/v) glucose added after cell growth | 1.6 | 1.7 |

TABLE 9

| Strain | Viscosity (cps at 3 rpm)$^a$ | |
|---|---|---|
|  | Untreated Fermentation Broth | 0.5% (w/v) Semi-pure Xanthan$^b$ |
| X59 | 440 | 370 |
| X59m9 | 680 | 430 |
| X50 | 770 | 720 |
| X50 del (c9e) | 790 | 750 |

$^a$Brookfield viscometer with spindle number 18.
$^b$Two volumes of isopropyl alcohol were added to fermentation broth to precipitate polysaccharides. The precipitate was dried, milled and resuspended at 0.5% (w/v) in 0.1% (w/v) NaCl.

EXAMPLE 7

Xanthan-Gum-Producing, Enzyme-Deficient Stains

As described in Example 1, we treated *X. campestris* strain X59 with a mutagen, ethylmethane sulfonate. Surviving bacteria were spread on agar plates (TBAB of Difco) that contained potato starch (1% w/v). After 2-3 days of growth at 30° C., colonies were screened by eye for those that were surrounded by a narrow or non-existent zone of clearing or "halo". A wide halo indicated normal digestion of the starch in the medium surrounding the colony by secreted amylase enzyme. Mutants defective in synthesis or secretion of active amylase would be expected to have a reduced size of halo. Three mutants were selected for further characterization. They were designated m60, m205 and m9. Mutant m60 showed no detectable halo, while mutants m205 and m9 had narrow halos compared to the parent strain X59. The three mutants also generated reduced halos on TBAB agar plates that contained carboxymethyl-cellulose (CMC). Thus the mutants appeared to secrete reduced levels of enzymes having amylase and cellulase activities.

The size of the halos on plates correlated with the results of assays of enzymes found in the supernatants of liquid cultures. The following table shows relative quantities of enzymes present in the culture broths.

TABLE 10

| Enzyme Activities in Culture Broths | | |
|---|---|---|
| Strain | Cellulase Activity[a] (Absorbance at 545 nm) | Amylase Activity[b] (Absorbance at 595 nm) |
| X59 | 0.16 | 0.76 |
| X59-m205 | 0.08 | 0.57 |
| X59-m9 | 0.09 | 0.34 |
| X59-m60 | 0.00 | 0.09 |

[a]Cells were grown overnight to early stationary phase in medium containing (per liter of tap water): 0.5 g casamino acids (Difco), 1 g potato starch, 1 ml glycerol, 1.6 g $(NH_4)_2SO_4$, 3.5 g $K_2HPO_4$, 2.6 g $KH_2PO_4$, 0.26 g $MgSO_4.7H_2O$, 6 mg $H_3BO_3$, 6 mg ZnO, 2.6 mg $FeCl_3.6H_2O$, 20 mg $CaCO_3$, and 0.13 ml 11.6 N HCl. Cells were removed from the culture supernatants by centrifugation. Each assay contained 0.1 ml of culture supernatant plus 0.1 ml of 1% (w/v) cellulose-azure type II from Sigma resuspended in phosphate-salt buffer (0.35% w/v $K_2HPO_4$, 0.16% w/v $KH_2PO_4$, 0.5 M NaCl. The assays were incubated for 48 hrs at room temperature without shaking in capped Eppendorf microtubes, and terminated by adding 0.8 ml 0.1 N HCl. Nonhydrolized substrate was removed by centrifugation and the absorbance of the supernatant was determined at 545 nm. The blue dye conjugated to the CMC is released into the supernatant by enzyme hydrolysis.
[b]Culture supernatants were prepared as for the cellulase assays. Each assay included 0.1 ml of culture supernatant plus 0.1 ml of 1% (w/v) amylose-azure from Sigma resuspended in phosphate-salt buffer as above. Incubation was for 16 hrs at room temperature without shaking in capped Eppendorf microtubes. The assays were terminated by adding 0.8 ml 0.1 N HCl and the absorbance measured at 595 nm.

In order to demonstrate utility for these enzyme-deficient mutants, we prepared xanthan gum from each, mixed the xanthan with CMC, and them measured the decrease of ciscosity of the CMC as a function of time. For CMC to be used as a thickening agent, it must maintain its viscosity in various formulations, for example in toothpaste. The results are tabulated below:

TABLE 11

| Viscosity of CMC in Mixtures with Xanthan Gum | | |
|---|---|---|
| | Viscosity of CMC[a] | |
| Source of Enzyme | 5 min | 20 min |
| 0.5 units Sigma cellulase | 270 | 136 |
| X59 | 705 | 395 |
| X59m205 | 670 | 310 |
| X59m9 | 730 | 395 |
| X59m60 | 932 | 870 |
| No addition | ca. 1000 | ca. 1000 |

[a]Cells were grown at 30° C. in shakeflasks containing (per liter of tap water): 10 g tryptone (Difco), 20 g glucose, 3.5 g $K_2HPO_4$, 2.6 g $KH_2PO_4$, 0.26 g $MgSO_4.7H_2O$, 6 mg $H_3BO_3$, 6 mg ZnO, 2.6 mg $FeCl_3.6H_2O$, 20 mg $CaCO_3$ and 0.13 ml 11.6 N HCl. The cultures were harvested within 48 hrs when the glucose was depleted and the culture had become viscous. The cultures were dilu ted with 2 volumes of fresh medium (lacking tryptone and glucose) and centrifuged to remove the cells. Then 2 volumes of isopropyl alcohol were added to precipitate the xanthan gum. The precipitate was dried, ground and resuspended at 0.5% (w/v) in 0.1 M NaCl to yield semi-purified xanthan gum. Semi-purified xanthan gum (0.25 ml or 125 μg) was added to 10 ml of 1% (w/v) CMC. The initial viscosity of the 1% (w/v) CMC solution was ca. 1000 cps as measured with a Brookfield LVT viscometer using spindle number 18 at 3 rpm at room temperature. Samples of xanthan gum containing cellulase enzyme were added and viscosity was determined as a function of time.

In a similar manner we measured the effect of xanthan gum samples prepared from strain X59 and mutant derivatives on the viscosity of starch as a function of time. Amylase activity contaminating the xanthan gum would be expected to degrade the starch and reduce its viscosity.

TABLE 12

| Viscosity of Starch in Mixtures with Xanthan Gum | | |
|---|---|---|
| Source of Enzyme[a] (Host Strain) | Xanthan Final Concentration (mg/ml) | Viscosity of Starch[b] |
| X59 | 0.00 | 1000 |
| | 0.25 | 715 |
| | 1.00 | 420 |

TABLE 12-continued

| Viscosity of Starch in Mixtures with Xanthan Gum | | |
|---|---|---|
| Source of Enzyme[a] (Host Strain) | Xanthan Final Concentration (mg/ml) | Viscosity of Starch[b] |
| | 1.75 | 272 |
| | 2.50 | 247 |
| X59m60 | 0.00 | 1000 |
| | 0.25 | 895 |
| | 1.00 | 550 |
| | 1.75 | 410 |
| | 2.50 | 420 |

[a]Samples of xanthan gum were prepared as described in Table 11. Xanthan gum was added to the final concentrations indicated. The starch solution was about 2% (w/v) potato starch in $H_2O$ and had been heat treated to solubilize.
[b]Viscosity was measured for the xanthan gum plus starch mixtures as described in Table 11, but at a single time, 1 minute after mixing.

These mutant strains are also useful as tools for the isolation of the structural genes that code for the enzymes. One can specifically mutate the enzyme-coding DNA and then introduce this mutation back into a nonmutagenized genetic background. For example, by creating deletions in the structural gene (or genes) one can completely eliminate these enzyme activities.

Figure 7:
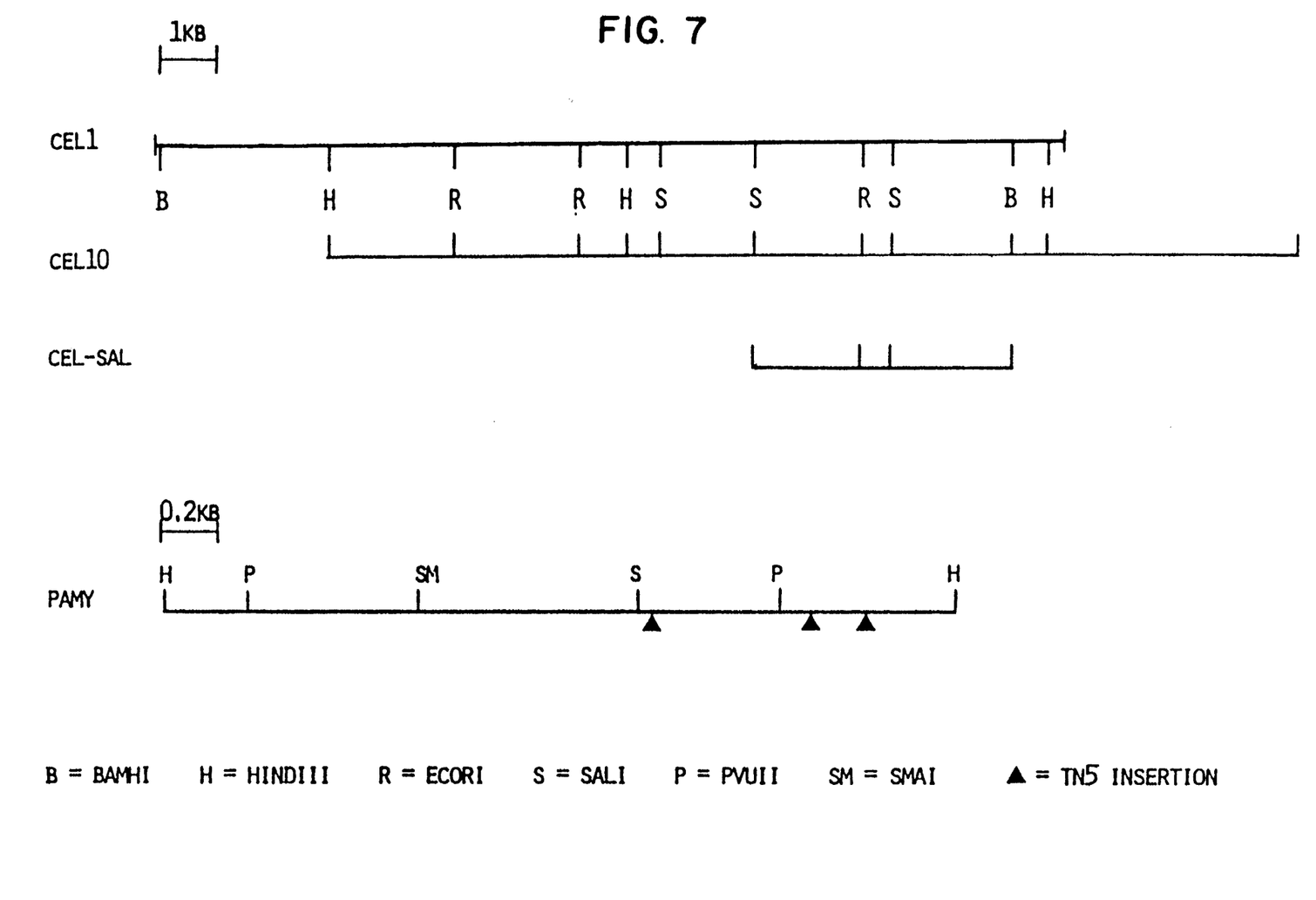
FIG. 7 is a restriction map of a number of genetic sequences used in preparing strains deficient in various externally secreted enzymes.

We have used two different approaches to isolating the genes coding for cellulase(s) and amylase(s). (There may be multiple genes for each as is the case for related species of bacteria.) In the first approach we did not use the enzyme-deficient mutants as the primary screening tool. Rather we took advantage of our observation that E. coli produced colonies that lacked halos on agar plates containing either amylose or cellulose. Thus these bacteria appeared analogous to our enzyme-deficient X. campestris. A library of genes from X. campestris was prepared in an E. coli host as described in Example 1. Colonies of E. coli containing recombinant plasmids were inspected on plates containing CMC or starch. A few colonies with halos of increased diameter were observed and selected for further characterization. From the CMC plates two clones were picked and designated as cel1 and cel10, and from the starch plates one colony named "patay" was selected. The two clones, cel1 and cel10, are overlapping in DNA sequence, as shown by mapping restriction sites (see FIG. 7). A subclone of cel1 and cel10 is also shown on the map and is designated cel-sal. This smaller piece of cloned X. campestris DNA retains the ability to cause E. coli to secrete cellulase into the medium surrounding colonies on agar plates. This results in the formation of a halo where the CMC has been digested and solubilized.

Either cel1 or cel10 plasmid clones cause strain X59 and its enzyme-deficient mutant derivatives to generate more cellulase activity in both periplasmic and extracellular (culture supernatant) fractions. The results for the supernatant activities are given in the following table.

TABLE 13

| | Cellulase Activities[b] | | | |
|---|---|---|---|---|
| | Host Strain | | | |
| Plasmid Clone[a] | X59 | X59m205 | X59m9 | X59m60 |
| cel1 | 0.55 | 0.32 | 0.40 | 0.06 |
| cel10 | 0.52 | 0.19 | 0.37 | 0.05 |
| A1 | 0.37 | 0.08 | 0.27 | 0.01 |

[a]Plasmids cel1 and cel10 carry overlapping segments of the X. campestris DNA. Clone A1 is included as a negative control and does not confer additional cellulase activity to its host. Each plasmid was transferred by conjugation to each host bacterium and cultures grown as described in Table 10.
[b]Cellulase activity in culture supernatants was determined as described in Table 10.

The pamy clone has also been mapped for restriction sites and the essential coding region determined by inactivation with transposon Tn5. The map is included on FIG. 7. The region that codes for the synthesis of amylase in hosts carrying this plasmid has been further mapped by Tn5 transposition. The sites of Tn5 insertion that inactivate the coding potential are indicated on the map.

The second approach to isolating the genes used the enzymedeficient mutants described previously as recipients for conjugation. The entire library of *X. campestris* cloned genes was mated from *E. coli* into X59m60. A few clones from the library complemented the narrow-halo phenotype of X59m60 on plates containing either CMC or starch, so that the exconjugants had normal sized halos. One clone, named celA2 was detected on CMC plates and one named amyD was isolated from starch plates.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. An isolated DNA sequence encoding genetic information controlling the synthesis of xanthan, said sequence having a restriction map of a segment selected from the group consisting of clH5, cl, c9H7, c82, c9, a fragment of C9H7 comprising c9e, a fragment of c82 comprising c9e, a fragment of c9 comprising c9e, and c9e.

* * * * *